US008822178B2

(12) United States Patent
Miles et al.

(10) Patent No.: US 8,822,178 B2
(45) Date of Patent: Sep. 2, 2014

(54) SWEETENER PREPARATIONS AND METHODS OF USE

(76) Inventors: Loren Miles, Los Angeles, CA (US); Michael Louie, Coralville, IA (US); Venkiteswaran Subramanian, Coralville, IA (US)

( * ) Notice: Subject to any disclaimer, the term of this patent is extended or adjusted under 35 U.S.C. 154(b) by 11 days.

(21) Appl. No.: 12/559,271

(22) Filed: Sep. 14, 2009

(65) Prior Publication Data

US 2010/0076176 A1 Mar. 25, 2010

Related U.S. Application Data

(60) Provisional application No. 61/096,753, filed on Sep. 12, 2008.

(51) Int. Cl.
*C12P 21/06* (2006.01)
*C07K 14/00* (2006.01)

(52) U.S. Cl.
USPC .......................................... 435/69.1; 530/350

(58) Field of Classification Search
None
See application file for complete search history.

(56) References Cited

U.S. PATENT DOCUMENTS

| | | | |
|---|---|---|---|
| 5,326,580 | A | 7/1994 | Hellekant et al. |
| 5,346,998 | A | 9/1994 | Hellekant et al. |
| 5,527,555 | A | 6/1996 | Hellekant |
| 5,741,537 | A | 4/1998 | Hellekant et al. |
| 6,274,707 | B1 | 8/2001 | Markley et al. |
| 7,153,535 | B2 | 12/2006 | Jin et al. |

FOREIGN PATENT DOCUMENTS

WO WO 99/25835 * 5/1999

OTHER PUBLICATIONS

Waterham et al. "Isolation of the *Pichia pastoris* glyceraldehyde-3-phophate dehydrogenase gene and regulation and use of its promoter", Gene, 1997, vol. 186, pp. 37-44.*

PGAPZ and PGAPZ-alpha A, B and C: Phicia expression vectors for constitutive expression and purification of recombinant proteins. Invitrogen Life Technologies, Version F (Sep. 3, 2002).*

PICZalpha A, B and C: Phicia expression vectors for selection on Zeocin and purificaiton of secreted, recombinant proteins. Invitrogen Life Technologies, Version E (Jan. 8, 2002).*

* cited by examiner

*Primary Examiner* — Suzanne M Noakes

(57) ABSTRACT

The present disclosure relates to codon-optimized brazzein coding sequences and the expression of brazzein and variants thereof using yeast expression systems. The disclosure also relates to methods of expression of proteins to enhance the sweetness taste profile of foods and/or beverages.

8 Claims, 6 Drawing Sheets

- P-GAL1: *GAL1* promoter regulates expression of MFα-brazzein
- P-GAL10: *GAL10* promoter, divergent from P-GAL1
- MFα: mating factor a secretion signal
- Brazzein-min: minor form of brazzein
- CYC1-TT: CYC1 transcription terminator
- pUC-ori: *E. coli* origin of replication
- Amp-R: Ampicillin resistant marker
- 2μ-ori: yeast origin of replication
- HIS3: yeast *HIS3* gene

SWEETENER PREPARATIONS AND METHODS OF USE

CROSS-REFERENCE TO RELATED APPLICATIONS

This application claims priority to U.S. Provisional Patent Application 61/096,753 filed on Sep. 12, 2008, the contents of which is incorporated herein by reference in its entirety.

FIELD OF THE INVENTION

Aspects and embodiments of the present disclosure relate in general to methods for making and using natural sweetener protein brazzein and variants thereof, including codon-optimized nucleic acid coding sequences, expression constructs, vectors, and host cells for the expression of brazzeins in yeast cells and/or other microbes. The disclosure also relates to novel methods for designing and testing microbial expression systems suitable for expressing brazzein proteins as sweeteners to enhance the sweet taste profile of foods and/or beverages.

BACKGROUND OF THE INVENTION

The following includes information that may be useful in understanding the present invention. It is not an admission that any of the information provided herein is prior art, or relevant, to the presently described or claimed inventions, or that any publication or document that is specifically or implicitly referenced is prior art.

Excessive consumptions of high-fructose corn syrup, artificial sweeteners, sugar, are linked to obesity, diabetes and numerous other health concerns. In the US, it is estimated that an average person consumes 20 teaspoons a day or more than 150 pounds of sugar per year. Teen consumption is even higher at 34 teaspoons of sugar a day. Excessive consumption of sugar has been linked to the recent dramatic rise in type 2 diabetes among adolescents. Further, as a result of excessive refining, sugar has low nutritional value as it is devoid of vitamins, minerals and fiber. It has been reported that 129 million adults in the U.S. are overweight and that over 60 million individuals (or over 30% of the adult population) are obese. As a result, 40 million children are overweight and these health conditions contribute to over 300,000 premature deaths each year.

Diabetes, however, is only one of the numerous consequences of sugar over-consumption. It has been reported that the detrimental effects of excess sugar in the diet go far beyond tooth decay and obesity. For example, sugar can cause irregularities in the insulin response; sugar can also cause diabetes-like damage to organs such as kidneys. It has been reported to contribute to the degeneration of the retina; and it raises blood lipid levels and increases the "adhesiveness" of the blood platelets, a common precursor of heart conditions.

The most effective way to achieve and sustain healthful weight-loss is by reducing calorie intake. Unfortunately, most individuals are instinctively attracted to the sensation of sweetness, which makes it more difficult for them to resist eating food and beverages which contain high-caloric, high-glycemic sugars and sweeteners such as, for example, sucrose, fructose, honey and high-fructose corn syrup. Further, food manufacturers that produce low- or reduced-fat products often substantially increase the sugar or sweetener content of their products to offset the loss of taste and texture often associated with reducing fat content.

One strategy in an attempt to solve these serious health issues is the creation of a zero- or low-calorie sweetener or sugar substitutes that can be used in foods and/or beverages to replace or reduce high-calorie sweeteners and/or sugar content. Examples of such zero-calorie artificial sweeteners include, for example, aspartame, acesulfame-K, sucralose and saccharin. Low-calorie natural sweeteners would include lo han guo and stevia both derived from fruit and roots, respectively. However, not all zero- or low-calorie sweeteners or sugar substitutes, artificial or natural are suitable for all applications. For example, some sweeteners may be suitable for beverages such as sodas and drink mixes but are not acceptable for use in baked goods because exposure to higher temperatures during baking can reduce the sweetening ability of the sweetener. Some natural sweeteners have a bitter aftertaste and do not render a sweet enough taste or exist in a natural color such as brown or yellow, which conflicts with clear beverages or light colored baked products. As another example, some sweeteners may be suitable for use in solid foods or baked goods but may not work properly for use in beverages and drink mixes due to limitations on solubility or may not have GRAS status (generally recognized as safe as defined by the FDA).

Thus, in light of the aforementioned, there is a clear need and a demand for an all-natural sweetener composition and methods for producing thereof that meets many of the health and commercial requirements.

Brazzein protein was first isolated from the fruit of *Pentadiplandra brazzeana* Baillon and has been reported to be multiple times sweeter than sucrose. There are at least two forms of brazzein identified in the fruit; the major form (about 80%), which has pyroglutamic acid at the N-terminus and the minor form (about 20%), which is identical to the major form except for the N-terminal residue, which is not pyroglutamic acid brazzein is heat-stable and its sweetness remains after heating at 80° C. for 4 hrs. The structure of brazzein contains one α-helix and three strands of antiparallel β-sheet. This stability of brazzein is due to four intramolecular disulfide bonds and the absence of no-free sulfhydryl groups in a brazzein molecule.

BRIEF SUMMARY OF THE INVENTION

The inventions described and claimed herein have many attributes and embodiments including, but not limited to, those set forth or described or referenced in this brief summary. It is not intended to be all-inclusive and the inventions described and claimed herein are not limited to or by the features or embodiments identified in this brief summary, which is included for purposes of illustration only and not restriction.

The present disclosure is directed to the surprising discovery that certain methods for brazzein protein production, including the use of codon-optimized nucleic acids in certain yeast expression systems, offer unexpected improvements and/or increase in efficiency, yield, taste profile, and/or thermostability.

The exemplary *Pichia* and *Sacharomyces* based yeast expression systems in the present disclosure offer unexpected economic (e.g. faster, easier) and production improvements (e.g. higher expression levels) as well as enhanced commercial characteristics (e.g. thermostable, favorable taste profile) for the production of brazzein over comparable prokaryotic, insect and mammalian tissue culture cell systems known to date. The exemplary yeast (i.e. single cell) expression systems described herein are easy to manipulate in culture and as a eukaryotes, these systems are capable of many of the post-translational modifications performed by higher eukaryotic cells such as proteolytic processing, folding, disulfide bond formation (important for thermostability), and glycosylation. In addition, certain brazzein proteins that end up as inactive inclusion bodies in bacterial expression systems are produced as biologically active molecules in the exemplary yeast expression systems (*P. pastoris* and *S. cerevisiae*) described herein. In certain embodiments, the exemplary yeast expression systems are also easier, and less expensive to use than expression systems derived from higher eukaryotes and usually gives higher expression levels.

In one embodiment, the present disclosure provides isolated nucleic acid molecules having the sequence of SEQ ID NOS: 1-2 and expression cassettes, vectors, and recombinant yeast host cells comprising these sequences. In certain embodiments, the yeast cells are *Pichia pastoris*. In certain other embodiments, the yeast cells are *Saccharomyces cerevisiae*.

In another aspect, the disclosure provides a method for preparing a thermostable brazzein comprising: expression in a yeast host cell an expression cassette comprising a promoter operably linked to a nucleic acid molecule encoding a brazzein polypeptide. In one embodiment, the method comprises a brazzein polynucleotide codon-optimized for expression in yeast host cell in a yeast expression system wherein the starting base sequence for codon-optimization is selected from any one of the following:

SEQ ID NO 7
```
  1 atggataagt gcaagaaggt ttacgaaaat tacccagttt ctaagtgcca acttgctaat
 61 caatgcaatt acgattgcaa gcttgataag catgctagat ctggagaatg cttttacgat
121 gaaaagagaa atcttcaatg catttgcgat tactgcgaat actaa 165
```

SEQ ID NO 8
```
  1 atggttaata gatctgttgc tttttctgct tttgttctta ttctttttgt tttggctatt
 61 tcagatattg cttctgtttc aggacaagat aagtgcaaga aggtttacga aaattaccca
121 gtttctaagt gccaacttgc taatcaatgc aattacgatt gcaagcttga taagcatgct
181 agatctggag aatgctttta cgatgaaaag agaaatcttc aatgcatttg cgattactgc
241 gaatactaa 249
```

SEQ ID NO 9
```
  1 atggctaagt ttgcttctat tattgctctt ttgtttgctg cacttgtttt gtttgctgca
 61 tttgaagctc caactatggt tgaagctcaa gataagtgca agaaggttta cgaaaattac
121 ccagtttcta agtgccaact tgctaatcaa tgcaattacg attgcaagct tgataagcat
181 gctagatctg gagaatgctt ttacgatgaa aagagaaatc ttcaatgcat ttgcgattac
241 tgcgaatact aa 252
```

SEQ ID NO 10
```
  1 atgagatttc cttctatttt tactgcagtt ttgttcgctg cctcttccgc tttggctcaa
 61 gataagtgta agaaggttta cgaaaattac ccagtttcta agtgccaact tgctaatcaa
121 tgcaattacg attgcaagct tgataagcat gctagatctg gagaatgctt ttacgatgaa
181 aagagaaatc ttcaatgtat ttgtgattac tgtgaatact aa 222
```

SEQ ID NO 11
```
  1 caggacaaat gtaaaaaagt atacgaaaac tacccggtat ccaaatgtca gctggcaaac
 61 cagtgtaact acgactgtaa actggacaaa cacgctcgtt ccggtgaatg cttctacgac
121 gaaaaacgta acctgcagtg catctgcgac tactgcgaat ac 162
```

SEQ ID NO 12
```
  1 cargayaart gyaaraargt ntaygaraay tayccngtnw snaartgyca rytngcnaay
 61 cartgyaayt aygaytgyaa rytngayaar caygcnmgnw snggngartg yttytaygay
121 garaarmgna ayytncartg yathtgygay taytgygart ay 162
```

SEQ ID NO 13
```
  1 gacaaatgca aaaaagttta cgaaaactac ccggtttcca aatgccagct ggctaaccag
 61 tgcaactacg actgcaaact ggacaaacac gctcgttccg gtgaatgctt ctacgacgaa
121 aaacgtaacc tgcagtgcat cggtgactac tgcggt 157
```

-continued

```
                                                  SEQ ID NO 14
  1 gayaartgya araargtnta ygaraaytay ccngtnwsna artgycaryt ngcnaaycar

 61 tgyaaytayg aytgyaaryt ngayaarcay gcnmgnwsng gngartgytt ytaygaygar

121 aarmgnaayy tncartgyat hggngaytay tgyggn 156

                                                  SEQ ID NO 15
  1 caggacaaat gtaaaaaagt atacgaaaac tacccggtat ccaaatgtca gctggcaaac

 61 cagtgtaact acgactgtaa actggacaaa cacgctcgtt ccggtgaatg cttctacgac

121 gaaaaacgta acctgcagtg catctgcgac tactgcgaat ac 162

                                                  SEQ ID NO 16
  1 cargayaart gyaaraargt ntaygaraay tayccngtnw snaartgyca rytngcnaay

 61 cartgyaayt aygaytgyaa rytngayaar caygcnmgnw snggngartg yttytaygay

121 garaarmgna ayytncartg yathtgygay taytgygart ay 162

                                                  SEQ ID NO 17
  1 gacaaatgca aaaaagttta cgaaaactac ccggtttcca aatgccagct ggctaaccag

 61 tgcaactacg actgcaaact ggacaaacac gctcgttccg gtgaatgctt ctacgacgaa

121 aaacgtaacc tgcagtgcat cggtgactac tgcggt 156

                                                  SEQ ID NO 18
  1 gayaartgya araargtnta ygaraaytay ccngtnwsna artgycaryt ngcnaaycar

 61 tgyaaytayg aytgyaaryt ngayaarcay gcnmgnwsng gngartgytt ytaygaygar

121 aarmgnaayy tncartgyat hggngaytay tgyggn 156
```

In another aspect, the disclosure provides a method for preparing a thermostable brazzein comprising: expression in a yeast host cell an expression cassette comprising a promoter operably linked to a nucleic acid molecule encoding a brazzein. In one embodiment, the brazzein protein comprises a polypeptide sequence selected from any one of the following:

```
                                                     SEQ ID NO 19
1 qdkckkvyen ypvskcqlan qcnydckldk harsgecfyd ekrnlqcicd ycey   54

                                                     SEQ ID NO 20
1 xdkckkvyen ypvskcqlan qcnydckldk harsgecfyd ekrnlqcicd ycex   54

                                                     SEQ ID NO 21
1 xdkckkvyen ypvskcqlan qcnydckldk harsgecfyd ekrnlqcicd ycex   54

                                                     SEQ ID NO 22
1 edkckkvyen ypvskcqlan qcnydckldk harsgecfyd ekrnlqcicd ycey   54

                                                     SEQ ID NO 23
1 dkckkvyeny pvskcqlanq cnydckldkh arsgecfyde krnlqcigdy cg     52

                                                     SEQ ID NO 24
1 edkckkvyen ypvskcqlan qcnydckldk harsgecfyd ekrnlqcicd ycey   54

                                                     SEQ ID NO 25
1 dkckkvyeny pvskcqlanq cnydckldkh arsgecfyde krnlqcigdy cg     52
```

In one embodiment, the brazzein retains at least 40% activity after 30 minutes at 60° C.

In certain embodiments, the disclosure also provides food or beverage sweetener comprising a thermostable brazzein produced by such methods.

In certain embodiments, the disclosure further provides a method of preparing a thermotolerant brazzein wherein the brazzein is glycosylated.

In certain embodiments, the disclosure also provides a glycosylated thermotolerant brazzein produced by such methods.

Aspects and embodiments of the present disclosure are used to provide natural, zero- or low-calorie natural sweetener, sweetener compositions, and preparations thereof that can be used in food products, including baked goods, snack goods, dairy goods and/or beverages and beverage mixes to replace or reduce high-calorie sugar or sugar sweetener content.

Aspects and embodiments of the present disclosure are also used to provide an all natural sweetener composition that tastes, bakes and cooks like sugar; is low-glycemic and/or diabetic-friendly; reduces the risk of tooth decay; contains less than 1 gram of carbohydrates per serving; and/or provides dietary supplementation.

Aspects and embodiments of the present disclosure are used to provide an all natural sweetener composition comprising a polyol, such as erythritol, an all natural sweetener agent comprised of a blend of oligofructose, fructose, vegetable protein isolate, and natural flavors, maltodextrin, isomaltulose (a low-calorie disaccharide derived from sucrose) and calcium. To achieve an enhanced baking performance nearly identical to that of cane sugar, natural, organic cane sugar (sucrose) may be added to the above referenced ingredients.

Accordingly, aspects and embodiments of the present disclosure are used to provide all natural sweetener composition comprising erythritol, a blend of oligo fructose, fructose, vegetable protein isolate, and natural flavors, maltodextrin, isomaltulose, calcium and natural cane sugar (sucrose).

Other objects and advantages will be apparent to those skilled in the art from the following description.

DETAILED DESCRIPTION

Figure 1A:
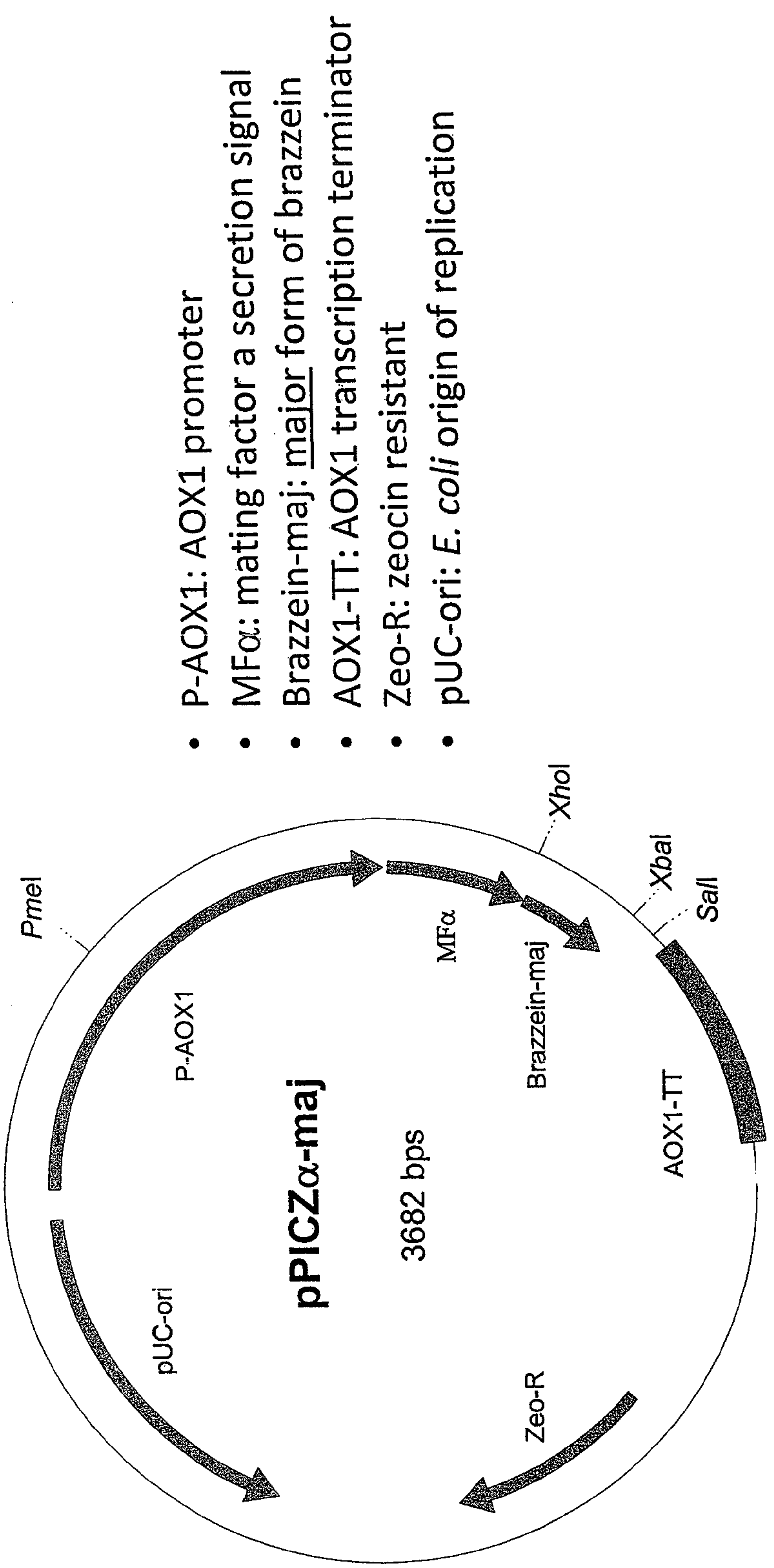
FIGS. 1A and 1B are the vector maps of an exemplary plasmid pPICZalpha suitable for the construction of an exemplary yeast expression vector for expressing brazzein in a yeast host cell (e.g. *Pichia pastoris*) constructed and operative in accordance with an embodiment of the present disclosure (vector 1A comprises an exemplary major form of brazzein; vector 1B comprises an exemplary minor form of brazzein).
Figure 1B:
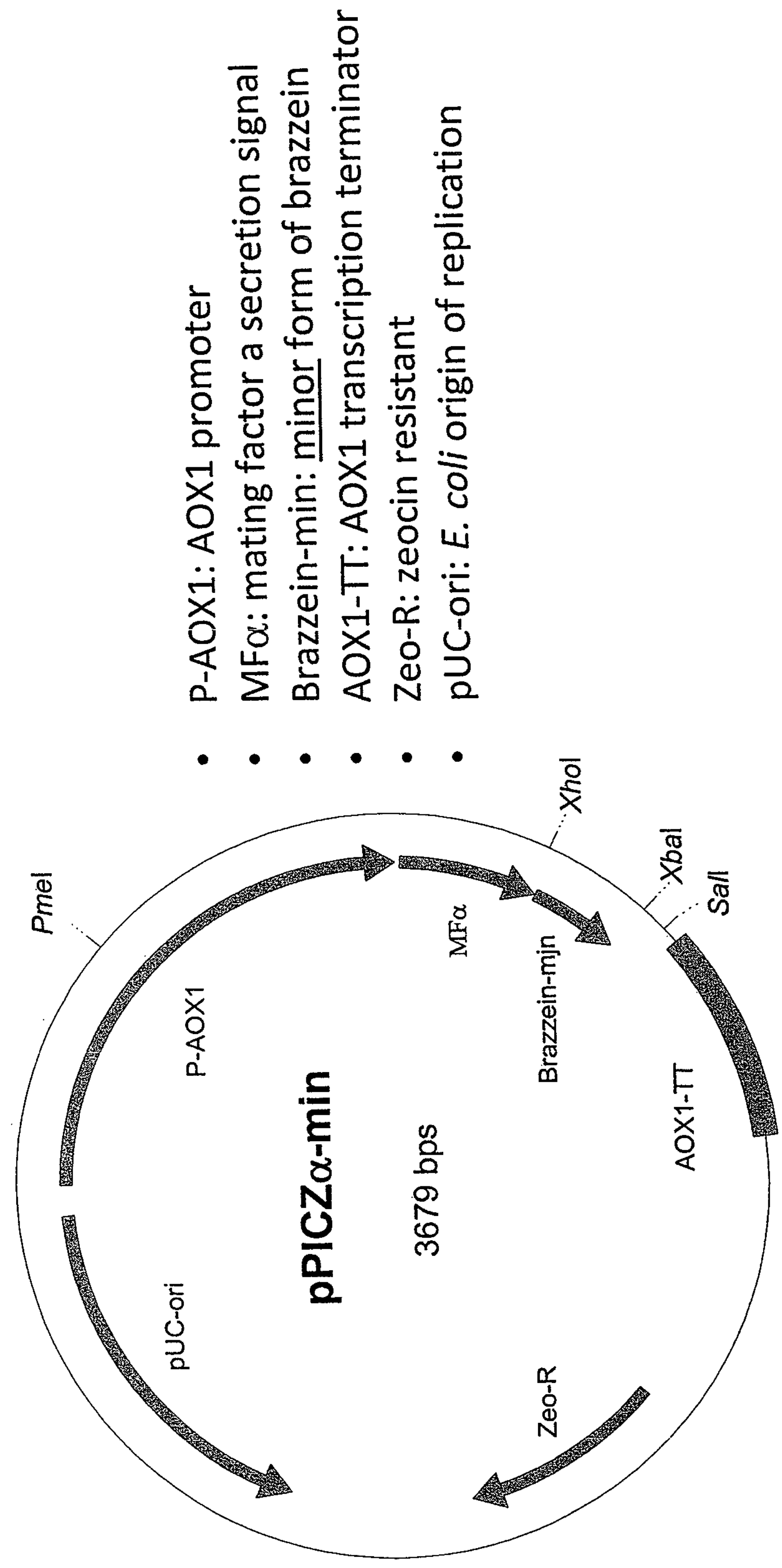
Figure 2A:
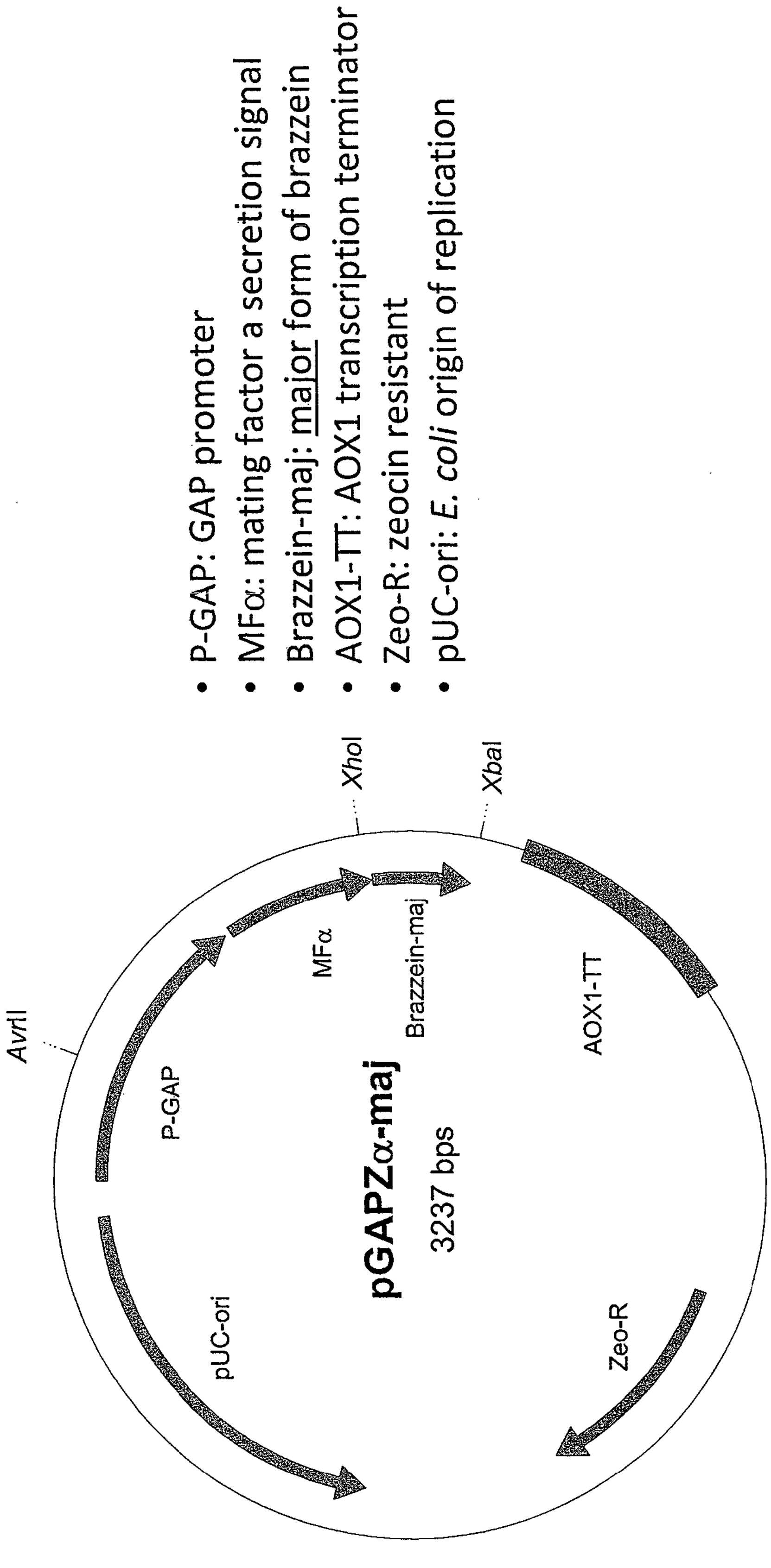
FIGS. 2A and 2B are the vector maps of an exemplary plasmid pGAPZalpha suitable for the construction of an exemplary yeast expression vector for expressing brazzein in a yeast host cell (e.g. *Pichia pastoris*) constructed and operative in accordance with the present disclosure (vector 2A comprises an exemplary major form of brazzein; vector 2B comprises an exemplary minor form of brazzein).
Figure 2B:
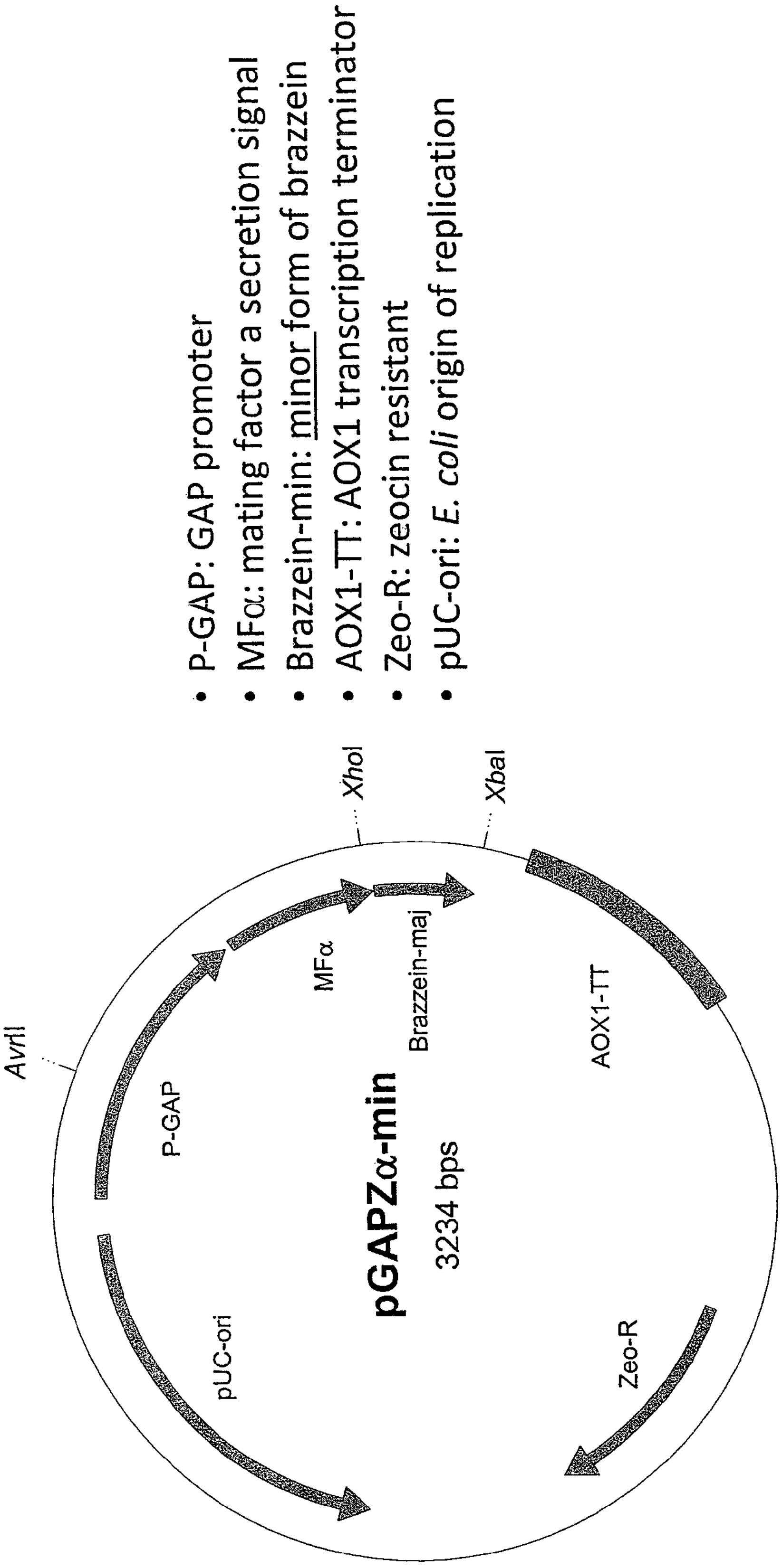
Figure 3A:
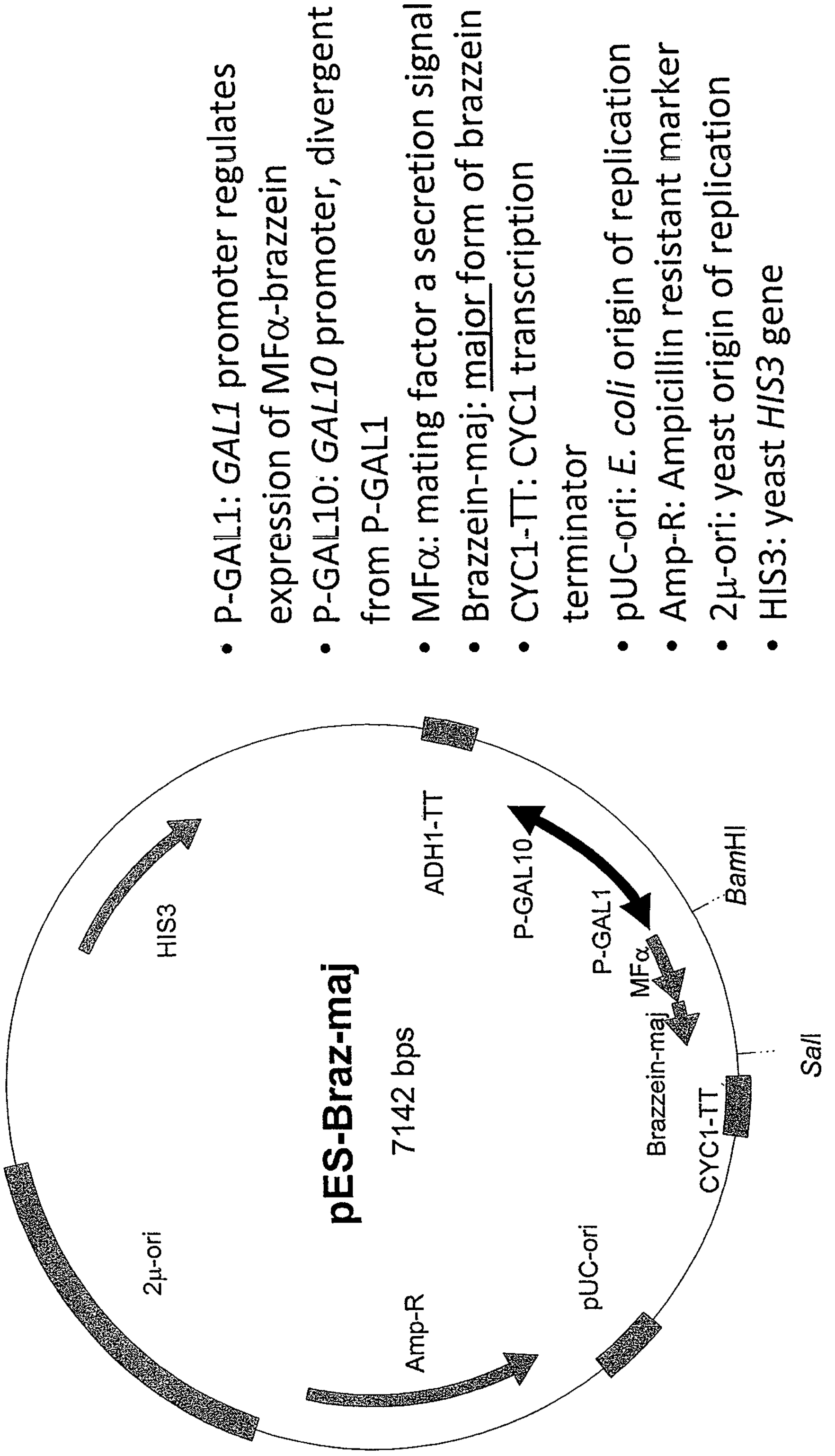
FIGS. 3A and 3B are the vector maps of an exemplary plasmid pESC suitable for the construction of an exemplary yeast expression vector for expressing brazzein in a yeast host cell (e.g. *Saccharomyces cerevisiae*) constructed and operative in accordance with the present disclosure (vector 3A comprises an exemplary major form of brazzein; vector 3B comprises an exemplary minor form of brazzein).
Figure 3B:
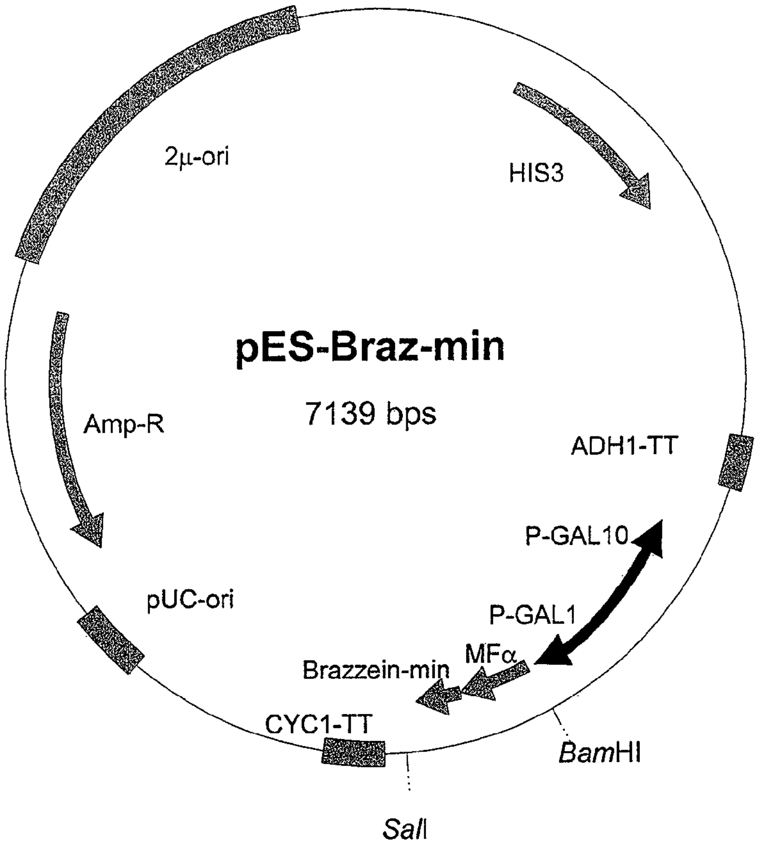

Aspects and embodiments of the disclosure will be set forth in part in the following description, unless otherwise defined, all technical and scientific terms and abbreviations used herein have the same meaning as commonly understood and known by one of ordinary skill in the art to which this invention pertains. Although methods and compositions similar or equivalent to those described herein can be used in practice of the present invention, suitable methods and compositions are described without intending that any such methods and compositions limit the invention herein.

General Aspects:

The present disclosure is directed to the surprising discovery that certain methods for brazzein protein production, including the use of codon-optimized nucleic acids in certain yeast expression systems, offer unexpected improvements and/or increase in efficiency, yield, taste profile, and/or thermostability.

The exemplary *Pichia* and *Sacharomyces* based yeast expression systems in the present disclosure offer unexpected economic (e.g. faster, easier) and production improvements (e.g. higher expression levels) as well as enhanced commercial characteristics (e.g. thermostable, favorable taste profile) for the production of brazzein over comparable prokaryotic, insect and mammalian tissue culture cell systems known to date. The exemplary yeast (i.e. single cell) expression systems described herein are easy to manipulate in culture; and as a eukaryotes, these systems are capable of many of the post-translational modifications performed by higher eukaryotic cells such as proteolytic processing, folding, disulfide bond formation (important for thermostability), and glycosylation. In addition, certain brazzein proteins that end up as inactive inclusion bodies in bacterial expression systems are produced as biologically active molecules in the exemplary yeast expression systems (*P. pastoris* and *S. cerevisiae*) described herein. In certain embodiments, the exemplary yeast expression systems for expressing brazzein in a yeast host cell are also easier, and less expensive to use than expression systems derived from higher eukaryotes and usually gives higher expression levels.

DEFINITIONS

Brazzein and Variants Thereof

Brazzein is a protein initially isolated from the fruit of *Pentadiplandra brazzeana* Baillon, and has been reported to be 500-2000 times sweeter than sucrose on a weight basis, and 9500 times sweeter on a molar basis (Ming and Hellekant; FEBS Lett. 1994 Nov. 21; 355(1):106-8). There are at least two forms of brazzein identified in the fruit; the major form (~80%), which has pyrogultamic acid at the N-terminus, has 54 amino acid residues. The minor form (~20%) is identical to the major form except for the N-terminal residue, which is not pyroglutamic acid. The molecular mass of brazzein is about 6.4 kDa. Brazzein is heat-stable and its sweetness remains after heating for example, 80° C. for 4 hours. This stability is related to the four intramolecular disulfide bonds and the absence of no-free sulfhydryl groups in a brazzein molecule. The structure of brazzein contains one α-helix and three strands of antiparallel β-sheet.

As used herein, exemplary suitable brazzein protein/polypeptides may comprise a sequence selected from any one of the following:

SEQ ID NO 7

```
  1 atggataagt gcaagaaggt ttacgaaaat tacccagttt ctaagtgcca acttgctaat

 61 caatgcaatt acgattgcaa gcttgataag catgctagat ctggagaatg cttttacgat

121 gaaaagagaa atcttcaatg catttgcgat tactgcgaat actaa 165
```

SEQ ID NO 8

```
  1 atggttaata gatctgttgc tttttctgct tttgttctta ttctttttgt tttggctatt

 61 tcagatattg cttctgtttc aggacaagat aagtgcaaga aggtttacga aaattaccca

121 gtttctaagt gccaacttgc taatcaatgc aattacgatt gcaagcttga taagcatgct
```

-continued

```
181 agatctggag aatgctttta cgatgaaaag agaaatcttc aatgcatttg cgattactgc

241 gaatactaa 249

                                                        SEQ ID NO 9
  1 atggataagt ttgcttctat tattgctctt ttgtttgctg cacttgtttt gtttgctgca

 61 tttgaagctc caactatggt tgaagctcaa gataagtgca agaaggttta cgaaaattac

121 ccagtttcta agtgccaact tgctaatcaa tgcaattacg attgcaagct tgataagcat

181 gctagatctg gagaatgctt ttacgatgaa aagagaaatc ttcaatgcat ttgcgattac

241 tgcgaatact aa 252

                                                       SEQ ID NO 10
  1 atgagatttc cttctatttt tactgcagtt ttgttcgctg cctcttccgc tttggctcaa

 61 gataagtgta agaaggttta cgaaaattac ccagtttcta agtgccaact tgctaatcaa

121 tgcaattacg attgcaagct tgataagcat gctagatctg gagaatgctt ttacgatgaa

181 aagagaaatc ttcaatgtat ttgtgattac tgtgaatact aa 222

                                                       SEQ ID NO 11
  1 caggacaaat gtaaaaaagt atacgaaaac tacccggtat ccaaatgtca gctggcaaac

 61 cagtgtaact acgactgtaa actggacaaa cacgctcgtt ccggtgaatg cttctacgac

121 gaaaaacgta acctgcagtg catctgcgac tactgcgaat ac 162

                                                       SEQ ID NO 12
  1 cargayaart gyaaraargt ntaygaraay tayccngtnw snaartgyca rytngcnaay

 61 cartgyaayt aygaytgyaa rytngayaar caygcnmgnw snggngartg yttytaygay

121 garaarmgna ayytncartg yathtgygay taytgygart ay 162

                                                       SEQ ID NO 13
  1 gacaaatgca aaaaagttta cgaaaactac ccggtttcca aatgccagct ggctaaccag

 61 tgcaactacg actgcaaact ggacaaacac gctcgttccg gtgaatgctt ctacgacgaa

121 aaacgtaacc tgcagtgcat cggtgactac tgcggt 156

                                                       SEQ ID NO 14
  1 gayaartgya araargtnta ygaraaytay ccngtnwsna artgycaryt ngcnaaycar

 61 tgyaaytayg aytgyaaryt ngayaarcay gcnmgnwsng gngartgytt ytaygaygar

121 aarmgnaayy tncartgyat hggngaytay tgyggn 156

                                                       SEQ ID NO 15
  1 caggacaaat gtaaaaaagt atacgaaaac tacccggtat ccaaatgtca gctggcaaac

 61 cagtgtaact acgactgtaa actggacaaa cacgctcgtt ccggtgaatg cttctacgac

121 gaaaaacgta acctgcagtg catctgcgac tactgcgaat ac 162

                                                       SEQ ID NO 16
  1 cargayaart gyaaraargt ntaygaraay tayccngtnw snaartgyca rytngcnaay

 61 cartgyaayt aygaytgyaa rytngayaar caygcnmgnw snggngartg yttytaygay

121 garaarmgna ayytncartg yathtgygay taytgygart ay 162

                                                       SEQ ID NO 17
  1 gacaaatgca aaaaagttta cgaaaactac ccggtttcca aatgccagct ggctaaccag

 61 tgcaactacg actgcaaact ggacaaacac gctcgttccg gtgaatgctt ctacgacgaa

121 aaacgtaacc tgcagtgcat cggtgactac tgcggt 156

                                                       SEQ ID NO 18
  1 gayaartgya araargtnta ygaraaytay ccngtnwsna artgycaryt ngcnaaycar

 61 tgyaaytayg aytgyaaryt ngayaarcay gcnmgnwsng gngartgytt ytaygaygar

121 aarmgnaayy tncartgyat hggngaytay tgyggn 156
```

As used herein, exemplary suitable brazzein protein/polypeptides may comprise a sequence selected from any one of the following:

```
                                              SEQ ID NO 19
1 qdkckkvyen ypvskcqlan qcnydckldk harsgecfyd ekrnlqcicd ycey   54

                                              SEQ ID NO 20
1 xdkckkvyen ypvskcqlan qcnydckldk harsgecfyd ekrnlqcicd ycex   54

                                              SEQ ID NO 21
1 xdkckkvyen ypvskcqlan qcnydckldk harsgecfyd ekrnlqcicd ycex   54

                                              SEQ ID NO 22
1 edkckkvyen ypvskcqlan qcnydckldk harsgecfyd ekrnlqcicd ycey   54

                                              SEQ ID NO 23
1 dkckkvyeny pvskcqlanq cnydckldkh arsgecfyde krnlqcigdy cg     52

                                              SEQ ID NO 24
1 edkckkvyen ypvskcqlan qcnydckldk harsgecfyd ekrnlqcicd ycey   54

                                              SEQ ID NO 25
1 dkckkvyeny pvskcqlanq cnydckldkh arsgecfyde krnlqcigdy cg     52
```

Sweetener Formulation and Composition for Food and Beverages:

As used herein, "baked food" or "baked good" comprises the all-natural sweetener compositions of the instant disclosure. "Baked goods" or "baked food products" can include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns. As used herein, "baked food or goods" can be classified into at least three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies; and muffins). Doughs generally are characterized as being flour-based, whereas batters are more water-based. In addition, "baked goods" generally comprise a combination of sweetener, water, and fat. Baked goods can also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon.

As used herein, the type of flour may be selected based on the desired food or baked goods product. Generally, the flour comprises an edible non-toxic flour that is conventionally utilized in baked goods. According to particular embodiments, the flour may be a bleached bake flour, general purpose flour, or unbleached flour. In other embodiments, flour may be enriched with additional vitamins, minerals, or proteins. Non-limiting examples of flours suitable for use in particular embodiments of the invention include wheat, corn meal, whole grain, fractions of whole grains (wheat, bran, and oatmeal), and combinations thereof. Starches or farinaceous material also may be used as the flour in particular embodiments. Common food starches generally are derived from potato, corn, wheat, barley, oat, tapioca, arrow root, and sago. Modified starches and pre-gelatinized starches also may be used in particular embodiments.

Baked goods may also comprise a number of additional conventional ingredients such as leavening agents, flavors, colors, milk, milk by-products, egg, egg by-products, cocoa, vanilla or other flavoring, as well as inclusions such as nuts, raisins, cherries, apples, apricots, peaches, other fruits, citrus peel, preservative, coconuts, flavored chips such as chocolate chips, butterscotch chips, and caramel chips, and combinations thereof. Leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

As used herein, taste improving compositions can impart positive affects on the taste profile can include elimination or reduction of the "undesirable taste," which includes any taste property which is not imparted by sugars, e.g. glucose, sucrose, fructose, or similar saccharides. Non-limiting examples of undesirable tastes include delayed sweetness onset, lingering sweet aftertaste, metallic taste, bitter taste, cooling sensation taste or menthol-like taste, licorice-like taste, and/or the like.

As used herein, the sweetener compositions of the instant disclosure can also be optionally combined if desired with additional "taste improving compositions." Exemplary components can include other carbohydrates, amino acids and their corresponding salts, polyamino acids and their corresponding salts, sugar acids and their corresponding salts, nucleotides, organic acids, inorganic acids, organic salts (including organic acid salts and organic base salts), inorganic salts, bitter compounds, flavorants and flavoring ingredients, astringent compounds, proteins or protein hydrolysates, surfactants, emulsifiers, flavonoids, alcohols, polymers, other sweet taste improving taste additives imparting such sugar-like characteristics, and combinations thereof.

As used herein "nutritive sweeteners" can include, for example, sucrose (table sugar), sugarcane; sugar alcohols; honey; fruits; syrups, including, for example, maple syrup, sugar beet syrup, corn syrup, cane syrup, golden syrup, barley malt syrup, molasses (treacle), brown rice syrup, and agave syrup.

As used herein, "non-nutritive sweeteners" can include, for example, Acesulfame potassium, also known as Sunett®; Alitame, also known as Aclame®; Aspartame, also known as Equal® or Nutrasweet®; Cyclamate; Glycyrrhizin; Lo han guo; Neotame; Nerillartine; Saccharin, also known as Sweet 'n' Low®; Stevioside; Sucralose, also known as Splenda®.

As used herein, "sugar" may include sucrose, lactose, and/or fructose.

As used herein, "polyol" (also known as "sugar alcohol", polyhydric alcohol, or polyalcohol) can be characterized in whole or in part by the presence of a hydrogenated form of carbohydrate, whose carbonyl group (e.g. aldehyde or ketone, reducing sugar) has been reduced to a primary or secondary hydroxyl group. Polyols have the general formula: $H(HCH0)_{n+1}H$, whereas sugar's is $H(HCH0)_nHCO$. Polyols do not contribute to tooth decay when used in food preparation as they are not metabolized by the bacteria in the mouth. In certain aspects, polyols can be used in combination with additional ingredients or agents which contribute complementary gygroscopic, crystalline, and/or heat of solution (warming effect when dissolved that helps cancel e.g. erythritol's cooling effect) characteristics. Exemplary sugar alcohols may include Glycol, Glycerol, Erythritol, Arabitol, Xylitol, Ribitol, Mannitol, Sorbitol, Isomalt, Maltitol, and Lactitol. In certain embodiments, erythritol is the preferred polyol. Disaccharides and monosaccharides can both form exemplary sugar alcohols; however, sugar alcohols derived from disaccharides (e.g. maltitol and lactitol) are not entirely hydrogenated because only one aldehyde group is available for reduction.

As used herein, the natural sweetener composition may comprise of a blend of oligofructose, fructose, vegetable protein isolate, and natural flavors (e.g. orange fruit peels).

Although natural caloric sweetener compositions, such as sucrose, fructose, and glucose, provide the most desirable taste to consumers, they are caloric in nature. Numerous natural and synthetic high-potency sweeteners are non-caloric; however, some exhibit sweet tastes that have different temporal profiles (e.g. onset, duration), maximal responses, flavor profiles, mouthfeels, and/or adaptation behaviors than that of sugar. It is well known to those skilled in the art of food/beverage formulation that optimal development of the sweetener in a composition requires re-balancing of the flavor and other taste components.

Thus, it is particularly desirable in the production of sweeteners and sugar substitutes to develop sweeteners and sweetener compositions that are as similar as possible to sugar in texture, taste, and usability. More specifically, it is particularly desirable to develop sweeteners and sweetener compositions that provide an appropriate level of sweetness, have an appropriate texture and mouthfeel, have a positive impact on product appearance, have limited or no negative aftertaste, and provide flavor enhancing and/or masking abilities, stability, and the ability to rise, caramelize (brown), and to provide a crust when baked, and to preserve and taste similar to cane sugar taste profile. However, due to the varying properties of different sweetening ingredients, it is often difficult to achieve as satisfactory of a result when combining such ingredients. This is generally believed to be due to the synergistic effects of mixing various sweetening compounds wherein the sweetness of the mixture is often greater than the apparent sweetness of the individual components.

General Aspects of Yeast Expression System for Brazzein Expression:

The present disclosure is directed to the surprising discovery that certain methods for brazzein protein production, including the use of codon-optimized nucleic acids in certain yeast expression systems, offer unexpected improvements and/or increase in efficiency, yield, taste profile, and/or thermostability.

In accordance with one aspect of the present disclosure, methods of preparing and using a nucleic acid molecule (including codon optimized polynucleotide) that encodes a brazzein is provided. The brazzein may be thermotolerant, but it is not necessarily thermotolerant. Hence, the disclosure also relates to methods of preparing and using a nucleic acid molecule that encodes a thermotolerant brazzein. As used herein, the stability of the thermotolerant brazzein can range from those which retain at least 40% of the sweetness activity after 30 minutes at about 60° C. to those which retain its sweetness after heating for example, 80° C. for 4 hours or higher. The method described and claimed herein can express brazzein that is a thermotolerant brazzein in the absence of glycosylation. Alternatively, the method described and claimed herein also encompasses expressing a thermotolerant brazzein that is glycosylated by the host.

The disclosure also provides methods of preparing brazzeins, including thermotolerant brazzeins. The method comprises expressing in a microbial host cell an expression cassette comprising a promoter operably linked to a nucleic acid molecule encoding a brazzein. The microbial host cell may be a yeast cell (e.g., *Saccharomyces, Schizosaccharomyces, Pichia* or *Hansenula*) or fungal (e.g., *Aspergillus* or *Trichoderma*) cell. In particular, the host cell is *Saccharomyces cerevisiae* or *Pichia pastoris*. The microbial cell employed to prepare the recombinant brazzein may yield a glycosylated form of the recombinant brazzein.

The invention also provides the method of preparing a thermotolerant brazzein wherein the brazzein is encoded by the nucleotide sequence of SEQ ID NOS: 7-18, or encoded by the polypeptide sequences of SEQ ID NOS: 19-25.

The disclosure further comprises a polynucleotide encoding the brazzein operably linked to at least one regulatory sequence, such as a promoter, an enhancer, an intron, a termination sequence, or any combination thereof, and, optionally, to a second polynucleotide encoding a signal sequence, which can direct the protein encoded by the first polynucleotide to a particular cellular location e.g., an extracellular location. Promoters can be constitutive promoters or inducible (conditional) promoters. As described herein, mutagenesis of a parent polynucleotide encoding a brazzein are employed to prepare variant (synthetic) DNAs encoding a brazzein having improved properties relative to the brazzein encoded by the parent polynucleotide. In an embodiment, brazzein proteins are screened for improved activity or improved expression level in host organisms. In another embodiment, the mutations in a number of the variant DNAs were combined to prepare a synthetic polynucleotide encoding a brazzein with enhanced thermotolerance relative to the brazzein encoded by the parent polynucleotide. A parent polynucleotide may be obtained from any source including plant, bacterial or fungal nucleic acid, and any method may be employed to prepare a synthetic polynucleotide of the invention from a selected parent polynucleotide, e.g., combinatorial mutagenesis, recursive mutagenesis and/or DNA shuffling.

Thus, in one embodiment of the disclosure, the thermotolerant brazzein has one or more amino acid substitutions relative to a corresponding brazzein, which substitutions are associated with the retention of activity at temperatures equal to or greater than 60° C. or higher.

In another embodiment, the disclosure provides a method for making a brazzein protein with enhanced thermotolerance due to glycosylation comprising expressing the protein in *Pichia pastoris* or *S. cerevisiae.*

In another embodiment, the disclosure provides a method for making a brazzein protein with enhanced sweetness activity or improved taste profile due to glycosylation comprising expressing the protein in *Pichia pastoris* or *S. cerevisiae.*

In another embodiment, an isolated nucleic acid molecule codon optimized for yeast cell expression is provided wherein the template for codon optimization comprises any one of the sequences of SEQ ID NOS: 7-18.

The disclosure also provides an expression cassette comprising a nucleic acid molecule comprising the nucleotide sequence of SEQ ID NOS: 1-2. In certain embodiments, the expression cassette is a yeast expression vector comprising the nucleic acid sequences of SEQ ID NOS: 7-18, or polynucleotides that encode the polypeptides of SEQ ID NOS: 19-25.

The exemplary expression cassette can further comprise an isolated nucleotide sequence encoding a secretion signal peptide, such as the *Saccharomyces cerevisiae* α-mating factor prepro-peptide secretion signal. The expression cassette can further comprise at least one nucleic acid molecule encoding a brazzein of the invention operably linked to a promoter.

The invention also provides recombinant host cells comprising at least one nucleic acid molecule of SEQ ID NOS: 7-18. The recombinant host cell can be a yeast or fungal cell. In particular the host cell is *Saccharomyces* and *Pichia*. In particular, the host cell is *Pichia pastoris* or *Saccharomyces cerevisiae.*

In a more particular embodiment, the host cell comprises the vector pPICZ alpha, pGAPZ alpha or pESC. In particular the host cell is *Pichia pastoris* comprising the vectors pPICZ alpha or pGAPZ alpha. In particular, the host cell is *Saccharomyces cerevisiae* comprising a pESC series of vectors (Invitrogen Ca.).

Also provided by the invention are vectors comprising the expression cassette or polynucleotide of the invention, and transformed microbial cells comprising the polynucleotide, expression cassette or vector of the invention. A vector of the invention can encode more than one polypeptide including more than one brazzein or may encode a fusion polypeptide comprising the brazzein of the invention, and a transformed microbial cell may comprise one or more vectors of the invention. The transformed cells of the invention are useful for preparing the brazzein of the invention. Accordingly, the invention provides brazzein isolated from the transformed microbial cells of the invention, as well as synthetically prepared protein. The invention also provides an isolated thermotolerant brazzein made by the method of the invention. Further, the isolated thermotolerant brazzein is glycosylated.

Constructs and Host Cells

The invention also provides an expression cassette comprising a nucleic acid sequence (promoter) capable of directing expression of a polynucleotide encoding a brazzein either in vitro or in vivo. Methods to prepare and/or identify a brazzein may include codon optimization and/or selection or screening, e.g., for brazzeins having enhanced activity at higher temperatures, improved sweetness, or better taste profile. General methods for nucleotide sequence alterations for codon optimization are well known in the art. One of ordinary skill in the art, with the teachings of the present invention, may arrive at all the possible combinations as contemplated herein for optimization of brazzein expression in a particular host cell.

DNA and Host Cells for Transformation

Vectors, plasmids, and isolated nucleic acid molecules for use in transforming cells will generally comprise the brazzein encoding nucleic acid molecules, as well as other nucleic acid molecules such as cDNA, gene or genes which one desires to introduce into the cells. These nucleic acid constructs can further comprise nucleic acid molecules such as promoters, enhancers, polylinkers, or even regulatory genes as desired. One of the nucleic acid molecules or genes chosen for cellular introduction will often encode a protein which will be expressed in the resultant transformed cells, such as will result in a screenable or selectable trait and/or which will impart an improved phenotype to the transformed cell.

Isolated nucleic acid molecules useful for introduction into cells comprise that which has been derived or isolated from any source that may be subsequently characterized as to structure size and/or function, chemically altered, and later introduced into cells. An example of an isolated nucleic acid molecule "derived" from a source would be a nucleic acid sequence that is identified as a useful fragment within a given organism, and which is then chemically synthesized in essentially pure form. An example of such a nucleic acid molecule "isolated" from a source would be a useful nucleic acid molecule sequence that is excised or removed from said source by chemical means, e.g., by the use of restriction endonucleases, so that it can be further manipulated, e.g., amplified, for use in the invention, by the methodology of genetic engineering. Such a nucleic acid molecule is commonly referred to as "recombinant." Therefore useful nucleic acid molecules comprise completely synthetic nucleic acid molecules, semi-synthetic nucleic acid molecules, nucleic acid molecules isolated from biological sources, and nucleic acid molecules derived from introduced RNA. Generally, the introduced nucleic acid molecule is not originally resident in the genotype which is the recipient of the nucleic acid molecule, but it is within the scope of the invention to isolate a gene from a given genotype, and to subsequently introduce multiple copies of the gene into the same genotype, e.g., to enhance production of a given gene product.

The selection of an appropriate expression vector will depend upon the yeast host cells. Yeast or fungal expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences.

Suitable vectors include by way of example: for yeast host cells: pPICZ, pGAPZ, and pESC. However, any other plasmid or vector may be used as long as they are replicable and viable in the host.

As representative examples of appropriate hosts may include, for example, yeast belonging to the genera *Kluyveromyces, Saccharomyces, Schizosaccharomyces, Trichosporon, Schwanniomyces, Pichia* and the like. If fungal cells are contemplated, fungal cells may include *Aspergillus, Rhizopus, Trichoderma, Neurospora, Mucor, Penicillium.* The construction of vectors which may be employed in conjunction with the present disclosure will be known to those of skill of the art in light of the present disclosure (see, e.g., Sambrook et al., *Molecular Cloning*, Cold Spring Harbor Press, 1989; Gelvin et al., *Plant Molecular Biology Manual,* 1990). The expression cassette of the invention may contain one or a plurality of restriction sites allowing for placement of the polynucleotide encoding a brazzein under the regulation of a regulatory sequence. The expression cassette may also contain a termination signal operably linked to the polynucleotide as well as regulatory sequences required for proper translation of the polynucleotide. The expression cassette containing the polynucleotide of the invention may be chimeric, meaning that at least one of its components is heterologous with respect to at least one of the other components. Expression of the polynucleotide in the expression cassette may be under the control of a constitutive promoter, inducible promoter, regulated promoter, viral promoter or synthetic promoter.

The expression cassette may include in the 5'-3' direction of transcription, a transcriptional and translational initiation region, the polynucleotide of the invention and a transcriptional and translational termination region functional in vivo and/or in vitro. The termination region may be native with the transcriptional initiation region, may be native with the polynucleotide, or may be derived from another source. The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences which may be a combination of synthetic and natural sequences.

The exemplary vectors used in the present invention may also include appropriate sequences for amplifying expression. A promoter is a nucleotide sequence that controls the expression of a coding sequence by providing the recognition for RNA polymerase and other factors required for proper transcription. As used herein, any promoter capable of expressing in yeast hosts can be used as the promoter. Examples thereof include methanol inducible promoters or MFa-1 promoter. In addition to the use of a particular promoter, other types of elements can influence expression of transgenes. In particular, introns have demonstrated the potential for enhancing transgene expression.

An enhancer is a DNA sequence which can stimulate promoter activity and may be an innate element of the promoter or a heterologous element inserted to enhance the level or tissue specificity of a particular promoter. An enhancer is capable of operating in both orientations (5' to 3' and 3'-5' relative to the gene of interest coding sequences), and is capable of functioning even when moved either upstream or downstream from the promoter. Both enhancers and other upstream promoter elements bind sequence-specific DNA-binding proteins that mediate their effects.

Vectors for use in accordance with the present invention may be constructed to include an enhancer element. Constructs of the invention will also include the gene of interest along with a 3' end DNA sequence that acts as a signal to terminate transcription and allow for the polyadenylation of the resultant mRNA.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure.

A variety of techniques are available and known to those skilled in the art for introduction of constructs into a cellular host. Transformation of microbial cells may be accomplished through use of polyethylene glycol, calcium chloride, viral infection, DEAE dextran, phage infection, electroporation and other methods known in the art. Transformation of fungus, in particular *Pichia*, may be accomplished according to "*Pichia* Protocols", in *Methods Mol. Biol*., Higgins, David R. and Cregg, James M.; Eds. (Humana, Totowa, N.J.) (1998). Introduction of the recombinant vector into yeasts can be accomplished by methods including electroporation, use of spheroplasts, lithium acetate, and the like. Any method capable of introducing DNA into animal cells can be used: for example, electroporation, calcium phosphate, lipofection and the like.

The invention will be further described by the following examples, which are not intended to limit the scope of the invention in any manner.

EXAMPLE 1

Cloning the brazzein gene into a *Pichia pastoris* expression plasmid and produce brazzein as a secretory protein by the recombinant *P. pastoris* strain.

Analysis of Brazzein DNA Sequence for Codon Optimization

The brazzein gene sequence is analyzed for codon-optimization for expression in yeast cells such as *P. pastoris* and/or *S. cerevisiae*. Codon Optimal brazzein sequence is synthesize for high expression in *P. pastoris* and *S. cerevisiae*. Candidate brazzein may include the major form,

```
                                                    SEQ ID NO 3
1 EDKCKKVYEN YPVSKCQLAN QCNYDCKLDK HARSGECFYD EKRNLQCICD YCEY 54
```

the minor form,

```
                                                    SEQ ID NO 4
1 DKCKKVYENY PVSKCQLANQ CNYDCKLDKH ARSGECFYDE KRNLQCICDY CEY 53
```

or variants and structural, functional analogs thereof.

Exemplary DNA sequences of the major form of brazzein (optimized for both *Pichia* and yeast) may include:

```
                                                         SEQ ID NO 1
  1 GAAGATAAGT GTAAGAAGGT TTACGAAAAC TACCCAGTTT CTAAGTGTCA ATTGGCTAAC

 61 CAATGTAACT ACGATTGTAA GTTGGATAAG CATGCTAGAT CTGGTGAATG TTTTTACGAT

121 GAAAAGAGAA ACTTGCAATG TATTTGTGAT TACTGTGAAT ACTAA 165
```

Exemplary DNA sequence of the minor form of brazzein (optimized for both *Pichia* and yeast) may include:

```
                                                   SEQ ID NO 2
  1 GATAAGTGTA AGAAGGTTTA CGAAAACTAC CCAGTTTCTA AGTGTCAATT GGCTAACCAA

 61 TGTAACTACG ATTGTAAGTT GGATAAGCAT GCTAGATCTG GTGAATGTTT TTACGATGAA

121 AAGAGAAACT TGCAATGTAT TTGTGATTAC TGTGAATACT AA 162
```

When the 2 genes are synthesized, nucleotides are added at the 5' end (ctcgagaaaaga) (SEQ ID NO:26) and 3' end (tctaga) of both genes to facilitate cloning. They will not alter the final brazzein protein sequences.

The 2 genes are cloned into the XhoI/XbaI sites of pPICZ alpha A and pGAPZ alpha A. Both forms of the genes are cloned 3' to and in-frame with a stretch of DNA sequence on the vector coding for a MF alpha secretion signal:

Expression of Brazzein as Secretory Protein by *P. Pastoris*

The brazzein gene are cloned into 2 different *P. pastoris* expression plasmids: pPICZ alpha and pGAPZ alpha Invitrogen). Both of these expression plasmids contain the MF alpha secretion signal which can direct secretion of brazzein out of *P. pastoris* cells. In pPICZ alpha, a methanol inducible promoter regulates the expression of brazzein. In pGAPZ alpha, expression of brazzein is constitutive. The methanol inducible promoter is a stronger promoter than the constitutive promoter and can result in higher level expression of recombinant protein. However, the *P. pastoris* inducible system has a requirement for pure oxygen during fermentation. On the other hand, fermentation of *P. pastoris* constitutive expression system can be sustained with normal air. It does not require feeding of methanol and therefore is suitable for manufacturing a protein for food application.

The brazzein gene (including those codon-optimized for *P. pastoris* & *S. cerevisiae*) variants are cloned into pPICZ alpha and pGAPZ alpha. PCR is used to amplify the brazzein gene and then ligated into pPICZ alpha and pGAPZ alpha. Appropriate restriction enzyme cutting sites are engineered into the PCR primers to facilitate cloning. The brazzein gene are cloned 3' to and in-frame with the MF alpha secretion signal located on pPICZ alpha and pGAPZ alpha. The MF alpha secretion signal are cleaved off by *P. pastoris* signal peptidases during protein secretion. This yields a brazzein protein that is completely identical to natural brazzein in protein sequence (i.e. no modification to brazzein protein sequence).

The recombinant plasmids are subjected to DNA sequencing to ensure no mutation is introduced into the brazzein coding sequence during cloning procedures. After that, plasmids are transformed into *P. pastoris* by electroporation. The recombinant plasmids are integrated into *P. pastoris* chromosome and stably maintained in *P. pastoris* genome. Transformants are selected on YPD agar plates with increasing concentrations of zeocin. Transformants resistant to high concentration of zeocin are indicative of integration of multiple copies of the plasmid into *P. pastoris* genome. High copy number often correlates to high protein expression level in *P. pastoris*.

Eight transformants from each expression construct that are resistant to high level of zeocin are chosen for shake-flask study. These transformants are grown in shake-flasks at 30° C. The 8 pPICZ alpha transformants are induced for brazzein production by adding methanol to the growth media daily. The induction is carried out over 3 days. The 8 pGAPZ alpha are grown for 2-3 days. brazzein is secreted out of *P. pastoris* cells in both types of transformants. Every day, samples are taken from these cultures for analyses. *P. pastoris* cells are removed by centrifugation and the spent media is analyzed for the presence of brazzein. Protein concentration in spent media is quantified by Bradford assay. Spent media containing a fixed amount of protein is loaded onto SDS-PAGE gels and analyzed for brazzein. Known amount of pure brazzein is loaded on the same SDS-PAGE gels and used as standard for estimation of brazzein level in the spent media. Recombinant *P. pastoris* strains that produce sufficient amount of brazzein are chosen for scale-up to purify larger quantity of brazzein protein.

EXAMPLE 2

Cloning the brazzein gene into a *Saccharomyces cerevisiae* expression plasmid and produce brazzein as a secretory protein by the recombinant *S. cerevisiae* strain.

After constructing the 4 *Pichia* expression plasmids, the 2 forms of MF alpha-brazzein (major form and minor form of brazzein) fusion gene is amplified from pPICZ alpha-maj and pPICZ alpha-min. The same pair of PCR primers will be used to amplify the forms of MF alpha-brazzein. Forward primer (5'-AACCCCGGATCCAAACGATGAGATTTCCTTC-3') (SEQ ID NO 5); reverse prime (5'-TGATG GTCGACGGCGCTATTCAGAT-3') (SEQ ID NO 6). The forward and reverse primers contain BamHI and SalI cut sites, respectively (underlined). The BamHI site on the forward primer is upstream to the start codon of the MF alpha secretion signal. The PCR products is cloned into the BamHI/SalI site of yeast expression plasmid pESCHIS.

Expression of Brazzein as Secretory Protein by *S. Cerevisiae*

The brazzein gene (including codon-optimized for *S. cerevisiae* and *P. pastoris*) is cloned into pESC-series of *S. cerevisiae* expression plasmid (Stratagene) to produce brazzein as secretory protein. Expression of brazzein as a *S. cerevisiae* internal protein may result in the modification of certain protein sequence (an additional methionine residue at the N-terminus of the recombinant brazzein protein) as the first amino acid in natural brazzein protein is not a methionine, which may be required to express brazzein internally. An ATG start codon (code for a methionine) is engineered into the 5' end of the brazzein gene.

PCR is used to amplify the MF alpha-brazzein fusion gene from the *P. pastoris* expression plasmid. The MF alpha-brazzein fusion gene is ligated into a pESC plasmid. Appropriate restriction enzyme cutting sites are engineered into the PCR primers to facilitate cloning. Expression of the MF alpha-brazzein gene are regulated by a galactose inducible promoter. During protein secretion out of *S. cerevisiae* cells, the MF alpha secretion signal is cleaved off by *S. cerevisiae* signal peptidase and will not result in any modification to the brazzein protein sequence.

The recombinant plasmid is subjected to DNA sequencing to ensure no mutation is introduced into the brazzein coding sequence during cloning procedures. After that, recombinant plasmid is transformed into a chosen strain of *S. cerevisiae* using S.c. EasyComp transformation kit (Invitrogen). This kit offers a simple method to rapidly produce highly competent *S. cerevisiae* cells. The transformation reaction mixture (plasmid DNA mix with competent cells) is plated on appropriate media and incubated for 3-5 days to allow the growth of transformant colonies. Selection of transformants is based on a nutritional marker on the expression plasmid. Thus, antibiotic is not needed to ensure maintenance of the expression plasmid inside *S. cerevisiae.*

Eight transformants are randomly chosen for a shake-flask study. These transformants are grown in shake-flasks at 30° C. and induced for protein production by adding galactose. The induction lasts for 1-3 days. Every day, an aliquot of each culture is sampled. The cells are removed by centrifugation and spent media is analyzed for brazzein. Recombinant strains that produce sufficient amount of brazzein is chosen for scale-up to purify larger quantity of brazzein protein.

EXAMPLE 3

Purification of Brazzein for Analysis

SDS-PAGE analyses are performed during expression study to monitor brazzein production by selected recombinant clones. brazzein expression level is estimated by comparing brazzein protein band intensity on SDS-PAGE gels to standard brazzein proteins loaded on the same gels. Bradford assay is performed to determine protein concentration after brazzein purification. Additional analytical assays, such as for example, determining the N-terminal sequence of brazzein and the MW of recombinant brazzein by MALDI-Mass Spectrometry are performed if needed.

One or multiple recombinant *P. pastoris* and/or *S. cerevisiae* clones is chosen for purification of recombinant brazzein. Since brazzein is a small 6.5-kDa protein and has been secreted out of the cells, a size-exclusion membrane filter is used to separate brazzein from other higher MW contaminating proteins. Since brazzein is a heat-stable protein, higher temperature is used to precipitate out contaminating proteins. Further purification is carried out by ion-exchange chromatography, hydroxyapatite chromatography, and size-exclusion chromatography as polishing step. Äkta chromatography systems suitable for both process development and production can be also be used.

While in the foregoing specification this invention has been described in relation to certain preferred embodiments thereof, and many details have been set forth for purposes of illustration, it will be apparent to those skilled in the art that the all natural sweetener composition according to this invention is susceptible to additional embodiments and that certain of the details described herein can be varied significantly without departing from the basic principles of the invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

While a particular embodiment of the invention has been shown and described, numerous variations and alternate embodiments will occur to those skilled in the art. Accordingly, it is intended that the invention be limited only in terms of the appended claims.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for preparing a brazzein protein, comprising:

expressing in a yeast host cell an expression vector comprising a promoter operably linked to a nucleic acid molecule encoding a brazzein polypeptide, wherein said nucleic acid molecule comprises a codon optimized sequence homolog selected from the group consisting of SEQ ID NO: 1 and SEQ ID NO: 2, and wherein said nucleic acid molecule is suitable for expression in *Pichia pastoris* or *Saccharomyces cerevisiae.*

2. An isolated nucleic acid molecule comprising a codon optimized sequence homolog that is selected from the group consisting of SEQ ID NO: 1 and SEQ ID NO: 2, and wherein said nucleic acid molecule is suitable for expression in *Pichia pastoris* or *Saccharomyces cerevisiae.*

3. An expression cassette comprising the nucleic acid molecule of claim 2.

4. A yeast expression vector comprising a nucleic acid molecule, wherein said nucleic acid molecule comprises a sequence selected from the group consisting of SEQ ID NO: 1 and SEQ ID NO: 2.

5. The expression cassette of claim 3, further comprising a nucleic acid molecule encoding a MF alpha secretion signal peptide.

6. An expression cassette comprising at least one nucleic acid molecule of claim 2, operably linked to a methanol inducible promoter.

7. A vector comprising at least one expression cassette of claim 6.

8. The vector of claim 7, wherein the vector comprises a plasmid selected from the group consisting of pPICZ alpha and pGAPZ alpha.

* * * * *

SEQUENCE LISTING

```
<160> NUMBER OF SEQ ID NOS: 26

<210> SEQ ID NO 1
<211> LENGTH: 165
<212> TYPE: DNA
<213> ORGANISM: Artificial Sequence
<220> FEATURE:
<223> OTHER INFORMATION: Exemplary sequence for major form of brazzein,
      optimized for both Pichia and yeast

<400> SEQUENCE: 1

gaagataagt gtaagaaggt ttacgaaaac tacccagttt ctaagtgtca attggctaac     60

caatgtaact acgattgtaa gttggataag catgctagat ctggtgaatg tttttacgat    120

gaaaagagaa acttgcaatg tatttgtgat tactgtgaat actaa                    165


<210> SEQ ID NO 2
<211> LENGTH: 162
<212> TYPE: DNA
```

-continued

```
<213> ORGANISM: Artificial Sequence
<220> FEATURE:
<223> OTHER INFORMATION: Examplary sequence for minor form of brazzein,
      optimized for both Pichia and yeast

<400> SEQUENCE: 2

gataagtgta agaaggttta cgaaaactac ccagtttcta agtgtcaatt ggctaaccaa     60

tgtaactacg attgtaagtt ggataagcat gctagatctg gtgaatgttt ttacgatgaa    120

aagagaaact tgcaatgtat ttgtgattac tgtgaatact aa                        162


<210> SEQ ID NO 3
<211> LENGTH: 54
<212> TYPE: PRT
<213> ORGANISM: Pentadiplandra brazzeana
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 3

Glu Asp Lys Cys Lys Lys Val Tyr Glu Asn Tyr Pro Val Ser Lys Cys
1               5                   10                  15

Gln Leu Ala Asn Gln Cys Asn Tyr Asp Cys Lys Leu Asp Lys His Ala
            20                  25                  30

Arg Ser Gly Glu Cys Phe Tyr Asp Glu Lys Arg Asn Leu Gln Cys Ile
        35                  40                  45

Cys Asp Tyr Cys Glu Tyr
    50


<210> SEQ ID NO 4
<211> LENGTH: 53
<212> TYPE: PRT
<213> ORGANISM: Pentadiplandra brazzeana

<400> SEQUENCE: 4

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50


<210> SEQ ID NO 5
<211> LENGTH: 31
<212> TYPE: DNA
<213> ORGANISM: Artificial Sequence
<220> FEATURE:
<223> OTHER INFORMATION: Forward primer for amplification of brazzein

<400> SEQUENCE: 5

aaccccggat ccaaacgatg agatttcctt c                                     31


<210> SEQ ID NO 6
<211> LENGTH: 25
<212> TYPE: DNA
<213> ORGANISM: Artificial Sequence
<220> FEATURE:
<223> OTHER INFORMATION: Reverse primer for amplification of brazzein

<400> SEQUENCE: 6
```

tgatggtcga cggcgctatt cagat 25

<210> SEQ ID NO 7
<211> LENGTH: 165
<212> TYPE: DNA
<213> ORGANISM: Artificial Sequence
<220> FEATURE:
<223> OTHER INFORMATION: nucleic acid molecule codon optimized for yeast cell expression

<400> SEQUENCE: 7
atggataagt gcaagaaggt ttacgaaaat tacccagttt ctaagtgcca acttgctaat 60
caatgcaatt acgattgcaa gcttgataag catgctagat ctggagaatg cttttacgat 120
gaaaagagaa atcttcaatg catttgcgat tactgtgaat actaa 165

<210> SEQ ID NO 8
<211> LENGTH: 249
<212> TYPE: DNA
<213> ORGANISM: Artificial Sequence
<220> FEATURE:
<223> OTHER INFORMATION: nucleic acid molecule codon optimized for yeast cell expression

<400> SEQUENCE: 8
atggttaata gatctgttgc tttttctgct tttgttctta ttctttttgt tttggctatt 60
tcagatattg cttctgtttc aggacaagat aagtgcaaga aggtttacga aaattaccca 120
gtttctaagt gccaacttgc taatcaatgc aattacgatt gcaagcttga taagcatgct 180
agatctggag aatgctttta cgatgaaaag agaaatcttc aatgcatttg cgattactgc 240
gaatactaa 249

<210> SEQ ID NO 9
<211> LENGTH: 252
<212> TYPE: DNA
<213> ORGANISM: Artificial Sequence
<220> FEATURE:
<223> OTHER INFORMATION: nucleic acid molecule codon optimized for yeast cell expression

<400> SEQUENCE: 9
atggctaagt ttgcttctat tattgctctt ttgtttgctg cacttgtttt gtttgctgca 60
tttgaagctc caactatggt tgaagctcaa gataagtgca agaaggttta cgaaaattac 120
ccagtttcta agtgccaact tgctaatcaa tgcaattacg attgcaagct tgataagcat 180
gctagatctg gagaatgctt ttacgatgaa aagagaaatc ttcaatgcat ttgcgattac 240
tgcgaatact aa 252

<210> SEQ ID NO 10
<211> LENGTH: 222
<212> TYPE: DNA
<213> ORGANISM: Artificial Sequence
<220> FEATURE:
<223> OTHER INFORMATION: nucleic acid molecule codon optimized for yeast cell expression

<400> SEQUENCE: 10
atgagatttc cttctatttt tactgcagtt ttgttcgctg cctcttccgc tttggctcaa 60
gataagtgta agaaggttta cgaaaattac ccagtttcta agtgccaact tgctaatcaa 120
tgcaattacg attgcaagct tgataagcat gctagatctg gagaatgctt ttacgatgaa 180
aagagaaatc ttcaatgtat ttgtgattac tgtgaatact aa 222

<210> SEQ ID NO 11
<211> LENGTH: 162
<212> TYPE: DNA
<213> ORGANISM: Artificial Sequence
<220> FEATURE:
<223> OTHER INFORMATION: nucleic acid molecule codon optimized for yeast
cell expression

<400> SEQUENCE: 11
caggacaaat gtaaaaaagt atacgaaaac tacccggtat ccaaatgtca gctggcaaac 60
cagtgtaact acgactgtaa actggacaaa cacgctcgtt ccggtgaatg cttctacgac 120
gaaaaacgta acctgcagtg catctgcgac tactgcgaat ac 162

<210> SEQ ID NO 12
<211> LENGTH: 162
<212> TYPE: DNA
<213> ORGANISM: Artificial Sequence
<220> FEATURE:
<223> OTHER INFORMATION: nucleic acid molecule codon optimized for yeast
cell expression
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t

<400> SEQUENCE: 12
cargayaart gyaaraargt ntaygaraay tayccngtnw snaartgyca rytngcnaay 60
cartgyaayt aygaytgyaa rytngayaar caygcnmgnw snggngartg yttytaygay 120
garaarmgna ayytncartg yathtgygay taytgygart ay 162

<210> SEQ ID NO 13
<211> LENGTH: 156
<212> TYPE: DNA
<213> ORGANISM: Artificial Sequence
<220> FEATURE:
<223> OTHER INFORMATION: nucleic acid molecule codon optimized for yeast cell expression

<400> SEQUENCE: 13
gacaaatgca aaaaagttta cgaaaactac ccggtttcca aatgccagct ggctaaccag 60
tgcaactacg actgcaaact ggacaaacac gctcgttccg gtgaatgctt ctacgacgaa 120
aaacgtaacc tgcagtgcat cggtgactac tgcggt 156

<210> SEQ ID NO 14
<211> LENGTH: 156
<212> TYPE: DNA
<213> ORGANISM: Artificial Sequence
<220> FEATURE:
<223> OTHER INFORMATION: nucleic acid molecule codon optimized for yeast cell expression
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t

<400> SEQUENCE: 14
gayaartgya araargtnta ygaraaytay ccngtnwsna artgycaryt ngcnaaycar 60
tgyaaytayg aytgyaaryt ngayaarcay gcnmgnwsng gngartgytt ytaygaygar 120
aarmgnaayy tncartgyat hggngaytay tgyggn 156

<210> SEQ ID NO 15
<211> LENGTH: 162
<212> TYPE: DNA
<213> ORGANISM: Artificial Sequence
<220> FEATURE:
<223> OTHER INFORMATION: nucleic acid molecule codon optimized for yeast cell expression

<400> SEQUENCE: 15
caggacaaat gtaaaaaagt atacgaaaac tacccggtat ccaaatgtca gctggcaaac 60
cagtgtaact acgactgtaa actggacaaa cacgctcgtt ccggtgaatg cttctacgac 120
gaaaaacgta acctgcagtg catctgcgac tactgcgaat ac 162

<210> SEQ ID NO 16
<211> LENGTH: 162
<212> TYPE: DNA
<213> ORGANISM: Artificial Sequence
<220> FEATURE:
<223> OTHER INFORMATION: nucleic acid molecule codon optimized for yeast cell expression
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (96)..(96)

<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t

<400> SEQUENCE: 16
cargayaart gyaaraargt ntaygaraay tayccngtnw snaartgyca rytngcnaay 60
cartgyaayt aygaytgyaa rytngayaar caygcnmgnw snggngartg yttytaygay 120
garaarmgna ayytncartg yathtgygay taytgygart ay 162

<210> SEQ ID NO 17
<211> LENGTH: 156
<212> TYPE: DNA
<213> ORGANISM: Artificial Sequence
<220> FEATURE:
<223> OTHER INFORMATION: nucleic acid molecule codon optimized for yeast cell expression

<400> SEQUENCE: 17
gacaaatgca aaaaagttta cgaaaactac ccggtttcca aatgccagct ggctaaccag 60
tgcaactacg actgcaaact ggacaaacac gctcgttccg gtgaatgctt ctacgacgaa 120
aaacgtaacc tgcagtgcat cggtgactac tgcggt 156

<210> SEQ ID NO 18
<211> LENGTH: 156
<212> TYPE: DNA
<213> ORGANISM: Artificial Sequence
<220> FEATURE:
<223> OTHER INFORMATION: nucleic acid molecule codon optimized for yeast cell expression
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t -continued
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t

<400> SEQUENCE: 18
gayaartgya araargtnta ygaraaytay ccngtnwsna artgycaryt ngcnaaycar 60
tgyaaytayg aytgyaaryt ngayaarcay gcnmgnwsng gngartgytt ytaygaygar 120
aarmgnaayy tncartgyat hggngaytay tgyggn 156

<210> SEQ ID NO 19
<211> LENGTH: 54
<212> TYPE: PRT
<213> ORGANISM: Artificial Sequence
<220> FEATURE:
<223> OTHER INFORMATION: exemplary brazzein protein

<400> SEQUENCE: 19

Gln Asp Lys Cys Lys Lys Val Tyr Glu Asn Tyr Pro Val Ser Lys Cys
1 5 10 15

Gln Leu Ala Asn Gln Cys Asn Tyr Asp Cys Lys Leu Asp Lys His Ala
20 25 30

Arg Ser Gly Glu Cys Phe Tyr Asp Glu Lys Arg Asn Leu Gln Cys Ile
35 40 45

Cys Asp Tyr Cys Glu Tyr
50

<210> SEQ ID NO 20
<211> LENGTH: 54
<212> TYPE: PRT
<213> ORGANISM: Artificial Sequence
<220> FEATURE:
<223> OTHER INFORMATION: exemplary brazzein protein
<220> FEATURE:
<221> NAME/KEY: misc_feature
<222> LOCATION: (1)..(1)
<223> OTHER INFORMATION: Xaa can be any naturally occurring amino acid
<220> FEATURE:

<221> NAME/KEY: misc_feature
<222> LOCATION: (54)..(54)
<223> OTHER INFORMATION: Xaa can be any naturally occurring amino acid

<400> SEQUENCE: 20

Xaa Asp Lys Cys Lys Lys Val Tyr Glu Asn Tyr Pro Val Ser Lys Cys
1 5 10 15

Gln Leu Ala Asn Gln Cys Asn Tyr Asp Cys Lys Leu Asp Lys His Ala
20 25 30

Arg Ser Gly Glu Cys Phe Tyr Asp Glu Lys Arg Asn Leu Gln Cys Ile
35 40 45

Cys Asp Tyr Cys Glu Xaa
50

<210> SEQ ID NO 21
<211> LENGTH: 54
<212> TYPE: PRT
<213> ORGANISM: Artificial Sequence
<220> FEATURE:
<223> OTHER INFORMATION: exemplary brazzein protein
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid

<400> SEQUENCE: 21

Xaa Asp Lys Cys Lys Lys Val Tyr Glu Asn Tyr Pro Val Ser Lys Cys
1 5 10 15

Gln Leu Ala Asn Gln Cys Asn Tyr Asp Cys Lys Leu Asp Lys His Ala
20 25 30

Arg Ser Gly Glu Cys Phe Tyr Asp Glu Lys Arg Asn Leu Gln Cys Ile
35 40 45

Cys Asp Tyr Cys Glu Xaa
50

<210> SEQ ID NO 22
<211> LENGTH: 54
<212> TYPE: PRT
<213> ORGANISM: Artificial Sequence
<220> FEATURE:
<223> OTHER INFORMATION: exemplary brazzein protein

<400> SEQUENCE: 22

Glu Asp Lys Cys Lys Lys Val Tyr Glu Asn Tyr Pro Val Ser Lys Cys
1 5 10 15

Gln Leu Ala Asn Gln Cys Asn Tyr Asp Cys Lys Leu Asp Lys His Ala
20 25 30

Arg Ser Gly Glu Cys Phe Tyr Asp Glu Lys Arg Asn Leu Gln Cys Ile
35 40 45

Cys Asp Tyr Cys Glu Tyr
50

<210> SEQ ID NO 23
<211> LENGTH: 52
<212> TYPE: PRT
<213> ORGANISM: Artificial Sequence
<220> FEATURE:
<223> OTHER INFORMATION: exemplary brazzein protein

<400> SEQUENCE: 23

-continued

```
Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Gly
        35                  40                  45

Asp Tyr Cys Gly
    50


<210> SEQ ID NO 24
<211> LENGTH: 54
<212> TYPE: PRT
<213> ORGANISM: Artificial Sequence
<220> FEATURE:
<223> OTHER INFORMATION: exemplary brazzein protein

<400> SEQUENCE: 24

Glu Asp Lys Cys Lys Lys Val Tyr Glu Asn Tyr Pro Val Ser Lys Cys
1               5                   10                  15

Gln Leu Ala Asn Gln Cys Asn Tyr Asp Cys Lys Leu Asp Lys His Ala
            20                  25                  30

Arg Ser Gly Glu Cys Phe Tyr Asp Glu Lys Arg Asn Leu Gln Cys Ile
        35                  40                  45

Cys Asp Tyr Cys Glu Tyr
    50


<210> SEQ ID NO 25
<211> LENGTH: 52
<212> TYPE: PRT
<213> ORGANISM: Artificial Sequence
<220> FEATURE:
<223> OTHER INFORMATION: exemplary brazzein protein

<400> SEQUENCE: 25

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Gly
        35                  40                  45

Asp Tyr Cys Gly
    50


<210> SEQ ID NO 26
<211> LENGTH: 12
<212> TYPE: DNA
<213> ORGANISM: Artificial Sequence
<220> FEATURE:
<223> OTHER INFORMATION: nucleotides added at 5' end of gene to
      facilitate cloning

<400> SEQUENCE: 26

ctcgagaaaa ga                                                          12
```